US010192715B2

(12) United States Patent
Renner

(10) Patent No.: US 10,192,715 B2
(45) Date of Patent: Jan. 29, 2019

(54) MEASUREMENT OF THE ELECTRIC CURRENT PROFILE OF PARTICLE CLUSTERS IN GASES AND IN A VACUUM

(71) Applicant: Bruker Daltonik GmbH, Bremen (DE)

(72) Inventor: Uwe Renner, Leipzig (DE)

(*) Notice: Subject to any disclaimer, the term of this patent is extended or adjusted under 35 U.S.C. 154(b) by 0 days.

(21) Appl. No.: 15/134,422

(22) Filed: Apr. 21, 2016

(65) Prior Publication Data

US 2016/0314932 A1   Oct. 27, 2016

(30) Foreign Application Priority Data

Apr. 27, 2015   (DE) .................. 10 2015 106 418

(51) Int. Cl.
| | |
|---|---|
| *H01J 37/244* | (2006.01) |
| *H01J 49/26* | (2006.01) |
| *H01J 49/00* | (2006.01) |
| *G01N 27/62* | (2006.01) |
| *H01J 49/02* | (2006.01) |

(52) U.S. Cl.
CPC .......... *H01J 37/244* (2013.01); *G01N 27/622* (2013.01); *H01J 49/0095* (2013.01); *H01J 49/025* (2013.01); *H01J 49/26* (2013.01); *H01J 2237/24405* (2013.01); *H01J 2237/24535* (2013.01)

(58) Field of Classification Search
None
See application file for complete search history.

(56) References Cited

U.S. PATENT DOCUMENTS

| 4,445,038 A * | 4/1984 | Spangler .............. G01N 27/622 250/287 |
| 5,401,965 A * | 3/1995 | Kaneko ............... H01J 49/0095 850/43 |
| 6,051,831 A * | 4/2000 | Koster .................. H01J 49/025 250/281 |
| 6,288,389 B1 * | 9/2001 | Franzen ............. H01J 49/0036 250/282 |
| 7,838,823 B1 | 11/2010 | Pfeifer et al. |
| 8,921,774 B1 * | 12/2014 | Brown .................... H01J 49/26 250/282 |

(Continued)

FOREIGN PATENT DOCUMENTS

DE   102009025727 A1   12/2010

*Primary Examiner* — Michael J Logie
(74) *Attorney, Agent, or Firm* — Benoit & Côté Inc.

(57) ABSTRACT

The invention relates to the measurement of current profiles of free-flying ion or electron clusters which impinge on a detector electrode of a Faraday detector. The detector electrode here consists of a large number of structural elements in a bipolar arrangement, where neighboring structural elements have opposite polarities and structural elements with the same polarity are electrically connected, and a voltage is applied between neighboring structural elements so that before ions or electrons impinge on the detection electrode, they are essentially deflected onto the structural elements with one of the two polarities. If the current profiles on the structural elements of the two polarities are measured separately and subtracted from each other, a current profile which corresponds to the pure ion or electron current profile is obtained without using a screen grid.

23 Claims, 4 Drawing Sheets

(56) References Cited

U.S. PATENT DOCUMENTS

| | | | | |
|---|---|---|---|---|
| 2004/0217294 A1* | 11/2004 | Zur | .................... | G01T 1/2018 |
| | | | | 250/370.09 |
| 2006/0027743 A1* | 2/2006 | Franzen | .................. | H01J 49/38 |
| | | | | 250/286 |
| 2006/0102852 A1* | 5/2006 | Williams | .................. | H05F 3/06 |
| | | | | 250/489 |
| 2006/0139252 A1* | 6/2006 | Lee | .................... | G09G 3/3241 |
| | | | | 345/76 |
| 2006/0226357 A1* | 10/2006 | Franzen | .................. | H01J 49/38 |
| | | | | 250/307 |
| 2007/0278402 A1* | 12/2007 | Zubarev | .................. | H01J 49/38 |
| | | | | 250/291 |
| 2009/0084948 A1* | 4/2009 | Baykut | .............. | G06Q 10/0633 |
| | | | | 250/282 |
| 2010/0181474 A1* | 7/2010 | Wang | .................. | H01J 49/0095 |
| | | | | 250/282 |
| 2014/0061458 A1* | 3/2014 | Baykut | .................. | H01J 49/38 |
| | | | | 250/282 |
| 2014/0217275 A1* | 8/2014 | Ding | .................... | H01J 49/027 |
| | | | | 250/282 |
| 2014/0340939 A1* | 11/2014 | Daly | .................... | H02M 1/40 |
| | | | | 363/17 |
| 2015/0115152 A1* | 4/2015 | Zhang | ................ | G01N 30/7206 |
| | | | | 250/288 |
| 2015/0185190 A1* | 7/2015 | Zhang | .................... | G01N 27/64 |
| | | | | 250/288 |
| 2016/0099137 A1* | 4/2016 | Brown | ................ | H01J 49/0036 |
| | | | | 250/290 |
| 2016/0141145 A1* | 5/2016 | Burchfield | ............ | H01J 37/244 |
| | | | | 250/281 |

* cited by examiner

MEASUREMENT OF THE ELECTRIC CURRENT PROFILE OF PARTICLE CLUSTERS IN GASES AND IN A VACUUM

BACKGROUND OF THE INVENTION

Field of the Invention

The invention relates to the measurement of the currents of free-flying electrically charged particles, such as ions or electrons, which impinge on a detector electrode of a Faraday detector, in ion mobility spectrometers, for example. The invention relates in particular to the prevention of signal distortions caused by induced image currents.

Description of the Related Art

The measurement of the electric currents of free-flying electrically charged particles such as electrons or ions by a planar detector electrode is distorted by the image currents which the approaching particles induce in the detector electrode. The distortion occurs in ion mobility spectrometers in particular and consists in a gradual increase of the ion signal, as is schematically depicted by the curves (6) and (7) in FIG. 1, which shows a schematic of an ion mobility spectrometer and a mobility spectrum. The order of magnitude of the mobility resolution is thus reduced by more than half. The distortion can be reduced in a known way by a (self-supporting) screen grid in front of the detector electrode, although in the case of miniaturized mobile devices with very fine screen grids in particular, strongly interfering microphonic effects occur. The screen grids also capture a portion of the particle current and thus reduce the sensitivity. The distortion of the particle trajectories caused by deflection at the screen grid reduces the mobility resolution. In addition, screen grids make up a considerable part of the production costs.

It is possible to obviate the need for a screen grid, as described in the patent specification U.S. Pat. No. 7,838,823 B1 by K. B. Pfeifer and A. N. Rumph entitled "Ion Mobility Spectrometer with Virtual Aperture Grid", by allowing charges to flow freely to the last electrodes of the field-generating electrode stack in the ion mobility spectrometer. These charges can partially compensate for the charge of the incoming ion cluster and thus reduce the image currents in the detector electrode, although they do not suppress them completely. The authors call this a "virtual grid".

There is still a need for better suppression of the distortion caused by the image currents, preferably without having to use a screen grid.

SUMMARY OF THE INVENTION

The invention provides a method which is used to measure the electric current profile (current-time curve, current curve) of free-flying clusters of electrically charged particles which impact on a detector electrode. The method is characterized by the fact that the detector electrode consists of a large number of structural elements in a bipolar arrangement, where neighboring structural elements have opposite polarities and all structural elements with the same polarity are connected together. A voltage is applied between the two groups of structural elements with different polarities so that shortly before the incoming particles impinge on the detector electrode, they are deflected in such a way that they hit only the structural elements of one polarity. The current profiles at the structural elements of both polarities are each measured separately and subtracted from each other. The image current profiles, which are formed in both groups of structural elements in practically the same way, are subtracted from each other and a current profile is obtained which corresponds to the pure particle current. The structural elements are arranged on a surface, in particular as a planar detector electrode.

Free-flying particles are deemed here to be, in particular, electrons or ions which move in a gas or vacuum, possibly under the influence of electric or magnetic fields. The free-flying particle clusters can be ions in a mobility spectrometer, for example, or also electrons which are generated by ions in a multichannel plate in a mass spectrometer. In the mobility spectrometer, the ions move in a gas at atmospheric pressure, for example, while the free-flying electrons are generated and measured at the operating pressure of the multichannel plate, i.e. usually in a high vacuum.

The method can be refined by applying a weighting as the two current profiles are subtracted. The current profiles can be measured and subtracted in analog electrical measurement electronics, by means of a differential amplifier (operational amplifier) after the current profiles have been converted into voltage signals, for example. The current profiles are usually pre-amplified before the conversion in this case. Another possibility consists in converting the analog current profiles (amplified, if necessary) into digital data with the aid of two analog-to-digital converters (A/D converters) and processing them further in an arithmetic logic unit. The amplifiers, differential amplifiers and A/D converters are preferably arranged on the back of a support whose front contains the structural elements of the detector electrode.

The detector electrode can have the form of a bipolar line grid, a pixel-like structure of squares or triangles, or a structure of concentric circles or concentric spirals (curved line grids) or a labyrinthine structure, for example.

The invention provides a Faraday detector to measure the electric current profile of clusters of electrically charged particles, said Faraday detector having a detection electrode whose detection surface borders on a gas-filled or evacuated space. The Faraday detector is characterized by the fact that the detector electrode consists of a large number of structural elements in a bipolar arrangement, where neighboring structural elements have opposite polarities and structural elements with the same polarity are electrically connected. The Faraday detector additionally has at least one voltage supply and one set of measurement electronics. The one or more voltage supplies are connected to the two groups of structural elements and supply the two groups of structural elements with different electric potentials such that particles originating from the space are essentially deflected onto the structural elements of one polarity. It is preferable for each group of structural elements to be connected to one power supply (DC voltage generator) in each case. The measurement electronics measure the current profiles at the structural elements with the two polarities separately.

A differential signal of the current profiles at the structural elements with the two polarities can be produced with the aid of a differential amplifier after a current-to-voltage conversion (I/U converter), for example. The measurement electronics can include the I/U converter, the differential amplifier and possibly one or more pre-amplifiers. The measurement electronics can, however, also comprise two analog-to-digital converters which convert the current profiles (amplified, where necessary) into two separate digital data streams, from which a differential signal is determined.

When measuring electron clusters, the space is usually at the operating pressure of secondary-electron multipliers (e.g., microchannel plates) in which the electron clusters are produced. The operating pressure is usually a high vacuum (p<0.1 Pa). For measuring ions in a mobility spectrometer, however, the pressure in the space can also be atmospheric pressure.

The detection electrode is preferably planar. It can, for example, have the form of a bipolar line grid, a pixel-like structure or a mosaic structure preferably of squares or triangles, or also a structure of concentric circles or concentric spirals (curved line grids) or a labyrinthine structure. The structural elements can be arranged on a support, but can also be mechanically self-supporting. The support can consist of an insulator (>$10^6$ Ohm·m) or have a high-resistance conducting ($10^2$-$10^6$ Ohm·m) surface. The width of the structures and separation of the structural elements are preferably less than 2000 µm, in particular less than 1000 µm, most preferably between 50 µm and 250 µm, but can also be less than 50 µm.

In a mobility spectrometer at atmospheric pressure, the electric fields for deflecting ions onto the structural elements with the same polarity are preferably less than 1000 V/cm, or at least significantly less than the breakdown field strength in the gas. To deflect charged particles in a vacuum, the requisite field strengths have to be approximately proportional to U/D, where U is the accelerating voltage traversed by the particles in front of the detection electrode, and D is the separation of neighboring structural elements of different polarities; the required field strengths depend on the separation of the structural elements and the kinetic energy with which particles impinge on the detector electrode. An accelerating voltage of U=500 V and a separation of D=0.5 mm results in a deflection field strength of 10,000 V/cm.

BRIEF DESCRIPTION OF THE DRAWINGS

The left-hand side of FIG. 1 shows a schematic of an ion mobility spectrometer but without gas circuit, sample introduction or electronics. Sample vapor is ionized in space (1), for example by electrons from a layer of radioactive nickel $^{63}$Ni.

An electric field generated by electric potentials at the stack (5) of ring electrodes pulls the ions to the gating grid (2), where they are mostly destroyed. The gating grid (2) can be a bipolar Bradbury-Nielsen shutter, for example. Opening the gating grid briefly allows a cloud of ions to enter the drift region. The cloud then dissolves into individual clusters (3) and (4) of ions with different mobility, which drift through the drift region when ions of different mobility are present. The ion clusters fly in a drift time of a few milliseconds at different drift speeds toward the detector electrode (10), generating image currents on the detector electrode (10) as they approach, before impinging on it. As they impinge, the ion clusters cancel out the surface charges produced by the image currents. The current profiles of the ion clusters are measured with the measuring device (13) and displayed as signals in the ion mobility spectrum, as shown on the right-hand side of FIG. 1. The image currents cause the signals of the mobility spectrum to become distorted by slowly rising slopes (6) and (7) and to have only a low mobility resolution.

As shown in FIG. 5, the individual ions are, however, deflected toward the electrodes connected to the measuring device (19) at the last moment. The two current diagrams (current profiles) on the left-hand side show the currents of the two measuring devices (19) and (20). The diagram top left shows the current $i_{i1}(t)$ at the electrodes on which the particles impinge. As has already been shown in FIG. 3, an image current profile (51) forms which corresponds only to the charge +q/2, however. At time $t_3$, when the first particles impinge on the electrodes, the neutralization of the image charge starts; only half the particle current is needed for this, however. The other half of the particle current flows away via the measuring device and results in the current profile (52) above the finely hatched area. The bottom diagram $i_{i2}(t)$ shows that an image current profile (53) is also formed in the electrodes to which no particle current flows. At time $t_3$, when the first particles impinge on the other electrodes and thus the charge of the cluster decreases, the image current decreases also, although further particles are still approaching the electrodes. As the charge in the cluster decreases, a portion of the image charge flows back. Curve (55) shows the build-up of the image charge if no charge were to flow back; curve (56) shows the return flow of the charge if there were no further build-up of the image charge. The result is the current profile represented by curve (57). This current profile, initially positive, later negative, is measured in the measuring device (20). Subtracting current profile $i_{i2}(t)$ from current profile $i_{i1}(t)$ gives the profile of the pure particle current $i_p(t)$, as shown in the diagram on the right.

DETAILED DESCRIPTION

The invention relates to the measurement of the currents of free-flying electric particles, such as ions or electrons, which impinge on a usually planar detector electrode, in ion mobility spectrometers, for example.

Figure 1:
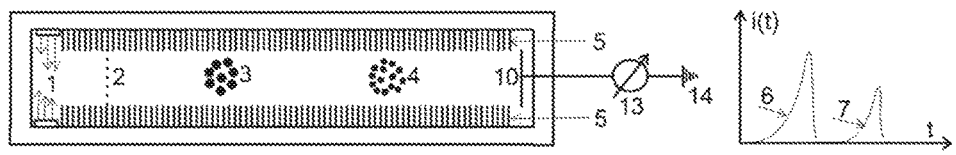

On the left-hand side of FIG. 1 is a schematic of such an ion mobility spectrometer but without gas circuit, sample introduction or electronics for a better understanding. Sample vapor is ionized in space (1), for example by electrons from a layer of radioactive nickel $^{63}$Ni. An electric field generated by electric potentials at the stack (5) of ring electrodes pulls the ions to the gating grid (2) where they are mostly destroyed. The gating grid (2) can be a bipolar Bradbury-Nielsen shutter, for example. Briefly opening the gating grid allows a small cloud of ions to enter the drift region. The cloud then separates into individual clusters (3) and (4) of ions with different mobility, which drift through the drift region at different speeds when ions of different mobility are present. The drift times are usually a few milliseconds. The ion clusters fly toward the detector electrode (10), generating image currents on the detector electrode (10) as they approach, before impinging on it. As they impinge, the ion clusters cancel out the surface charges produced by the image currents. The current profiles of the ion clusters are measured with the measuring device (13) and displayed as signals in the ion mobility spectrum, as shown on the right-hand side. The image currents cause the signals of the mobility spectrum to become distorted by slowly rising slopes (6) and (7) and to have only a low mobility resolution.

The invention relates in particular to the prevention of these ion signal distortions caused by induced image currents without using screen grids. To understand the invention, it is necessary to have a detailed understanding of the structure and behavior of the image currents.

Figure 2:
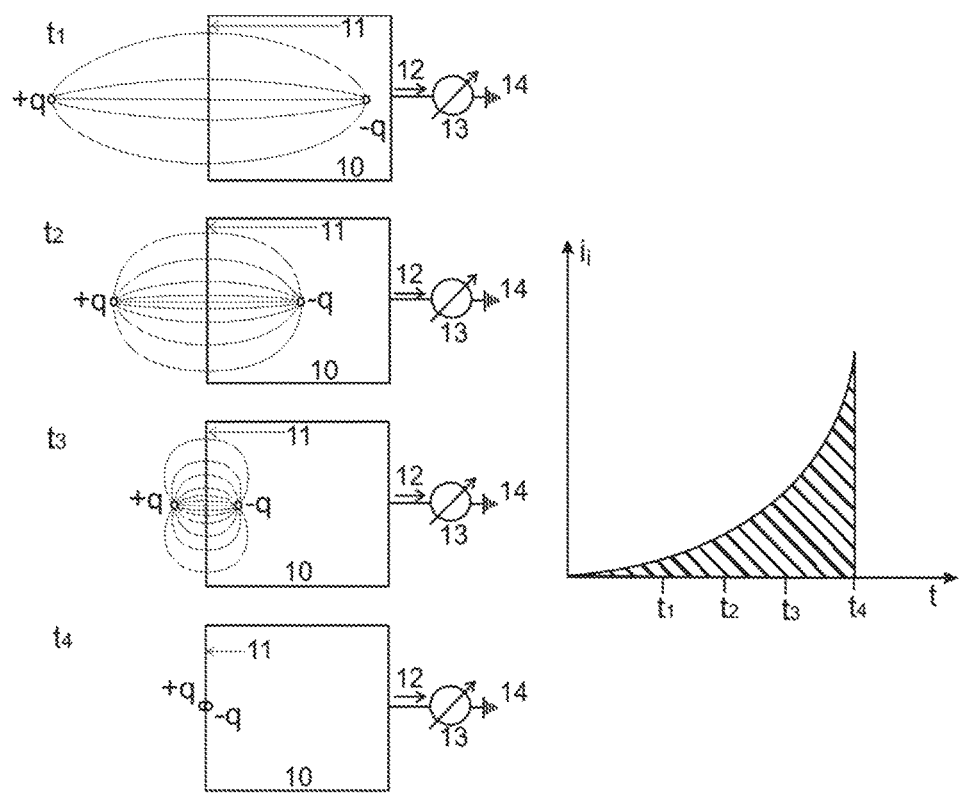
FIG. 2 shows how the measurement signal of a positive point charge +q is distorted by image currents. The left-hand side of the figure shows four stages ($t_1$-$t_4$) of the approach of the point charge +q to the detector electrode (10), one below the other. As is customary, the effect of the image currents can be depicted by imagining a virtual mirror charge −q, which is located at the same distance on the other side of the detector surface (11). In reality, a layered charge distribution forms on the detector surface (11) and generates a potential distribution corresponding to the mirror charge −q. While the charge for this layered charge distribution is building up, a negative current flows in the direction opposite to the arrow (12) (i.e., a positive current in the direction of the arrow) from the charge reservoir (14) to the detector electrode (10). This current is displayed and measured in the measuring device (13) as a positive current. The right-hand side shows the image current $i_i(t)$ as a function of time, i.e. over the course of stages $t_1$ to $t_4$. It increases as the point charge +q gets closer and closer to the detector surface (11). The sum of the charges −q built up on the surface (11) by the image currents corresponds increasingly to the charge +q of the point charge, but with opposite sign. The charge distribution contracts more and more to a point on the surface (11), the closer it gets to this surface. At the moment $t_4$ of the contact with the surface, this image charge −q is exactly neutralized by the point charge +q, and consequently current suddenly ceases to flow through the measuring device (13). The time integral over the image current $i_i(t)$, i.e. the hatched area in the diagram on the right-hand side, gives exactly the charge +q of the point charge. The current curve does not correspond to a delta function, however, as would be expected for the real current curve of a point charge, but corresponds to the increasing and suddenly ending current curve of diagram $i_i(t)$ on the right-hand side of the figure.

FIG. 2 shows how the measurement signal measured by the measuring device (13) of a positive point charge +q moving toward the detector electrode (10) and finally impinging on it, is distorted by image currents. The left-hand side of the Figure shows four stages $t_1$ to $t_4$ of the approach of the point charge +q to the detector electrode (10), one below the other. As is customary, the effect of the image currents can be depicted by imagining a virtual mirror charge −q, which is located at the same distance on the other side of the detector surface (11). In reality, a layered charge distribution forms on the detector surface (11) and generates a potential distribution corresponding to the mirror charge −q. While the charge for this layered charge distribution is building up, a current of negative charge carriers (electrons for example) flows in the direction opposite to the arrow (12) from the common ground (14) to the detector electrode (10). This current of negative charge carriers is displayed and measured in the measuring device (13) as a positive current. The diagram on the right-hand side of FIG. 2 shows this image current $i_i(t)$ as a function of time, i.e. over the course of stages $t_1$ to $t_4$. It increases as the point charge +q gets closer and closer to the detector surface (11). The sum of the charges −q built up on the surface (11) by the image currents corresponds increasingly to the charge +q of the point charge, but with opposite sign. The charge distribution contracts more and more to a point on the surface (11), the closer it gets to this surface. At the moment $t_4$ of the contact with the surface, this image charge −q is exactly neutralized by the point charge +q, and consequently current suddenly ceases to flow through the measuring device (13). The time integral over the image current $i_i(t)$, i.e. the hatched area in the diagram on the right-hand side, gives precisely the charge +q of the point charge. The measured current curve does not correspond to a delta function, however, as would be expected for the real current curve of a point charge, but corresponds to the increasing and suddenly ending current curve of diagram $i_i(t)$ on the right-hand side of the figure.

Figure 3:
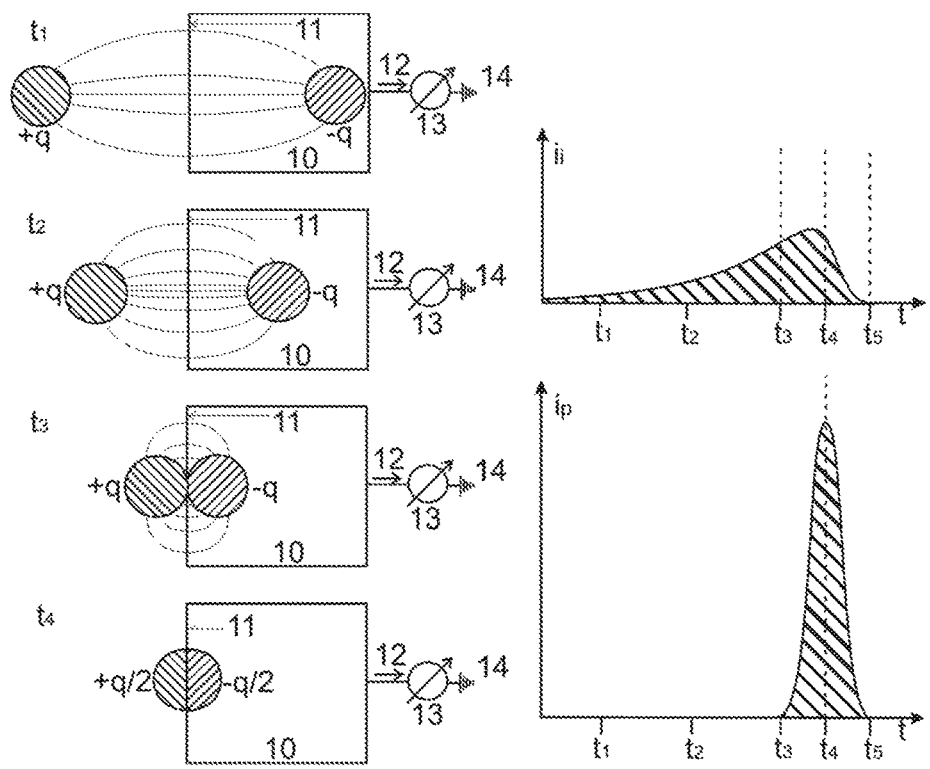
FIG. 3 illustrates an analogous process, not for a point charge, but for a spatially extended ion cluster, as exists in the ion mobility spectrometer according to FIG. 1, for example. At the top right-hand side of the figure is a diagram of the current curve $i_i(t)$ as measured by the measuring device (13). Here, also, the current curve $i_i(t)$ is distorted by the gradual build-up of the image charge on the surface (11), but it does not stop suddenly, because the neutralization process brought about by the cluster of incoming ions is spread out in time. The $i_i(t)$ curve is a superposition of temporally shifted current curves from FIG. 2, with a weighting which corresponds to the charge distribution in the cluster. The neutralization starts with the arrival of the first particle at time $t_3$. The particle current starts to neutralize the image charge, although an image current is still flowing through the measuring device (13), since most of the particles are still approaching. The current through the measuring device (13) ends precisely at the time t=$t_5$. The complete cluster of particles has now arrived at the detector electrode. The diagram $i_p(t)$ drawn at the bottom right shows what the current of the ions passing through the surface (11) would look like if there were no image current and no image charge, and thus no neutralization either. This current $i_p(t)$ can unfortunately not be measured directly; it is not registered by the measuring device (13). The objective of this invention is to derive precisely this current $i_p(t)$.

The current curve looks slightly different when an elongated cluster of charge carriers with a total charge +q approaches the detector electrode (10) and ultimately impinges on it. FIG. 3 illustrates such a process with an elongated ion cluster, as occurs in the ion mobility spectrometer according to FIG. 1, for example. Four stages $t_1$ to $t_4$ of the approach are again considered. The top right-hand side of the figure shows a diagram of the current curve $i_i(t)$ as measured by the measuring device (13). Here also, the current curve $i_i(t)$ is characterized by the gradual build-up of the image charge on the surface (11), but it does not stop suddenly, because the neutralization process brought about by the cluster of incoming ions is spread out in time. The $i_i(t)$ curve is a superposition of temporally shifted current curves from FIG. 2, which are weighted according to the charge distribution in the cluster. The neutralization starts at time $t_3$ with the arrival of the first ions on the detector surface (11). The ion current immediately starts to neutralize the image charge, although an image current is still flowing through the measuring device (13), since most of the ions are still approaching. The current through the measuring device (13) ends only at time $t=t_5$. The complete ion cluster has then arrived at the detector electrode.

In contrast to the current curve $i_i(t)$, the diagram $i_p(t)$ drawn at the bottom right shows how the ion current of the ions passing through the surface (11) would look if there were no image current and no image charge and thus no neutralization either. This current $i_p(t)$ can unfortunately not be measured directly; it is not registered by the measuring device (13). The objective of this invention is to represent precisely this current $i_p(t)$.

The two current curves $i_i(t)$ and $i_p(t)$ contain the same amount of charge, as represented by the hatched areas. By comparing the two curves, it is possible to determine that the current curve $i_i(t)$ measured in the measuring device (13) has a full width at half-maximum which is more than twice as large as that of the ion current $i_p(t)$. Therefore, if it is possible to measure this ion current without the distortion, the mobility resolution will more than double. Furthermore, the sensitivity, which is defined as signal amplitude over noise, increases for the same background noise, as can be seen from the height of the ion current curve, which is more than double.

Figure 4:
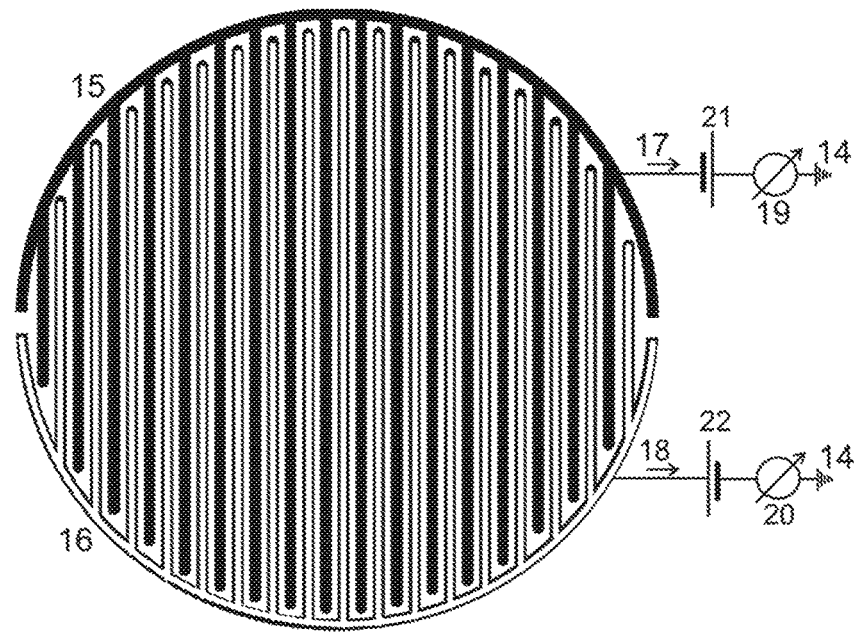
FIG. 4 shows a bipolar line grid as can be used for the invention. Such a line grid can be applied to a circuit board, for example. The linear electrodes of the two groups are connected together in each case; the voltage supplies (21) and (22) can apply different potentials to the electrodes of the two groups. The measuring devices (19) and (20) can measure the currents between the groups of electrodes and a common ground (14), without being able to distinguish between image currents and the electric currents of the particles. The directional arrows (17) and (18) indicate the direction of positive currents.
Figure 7:
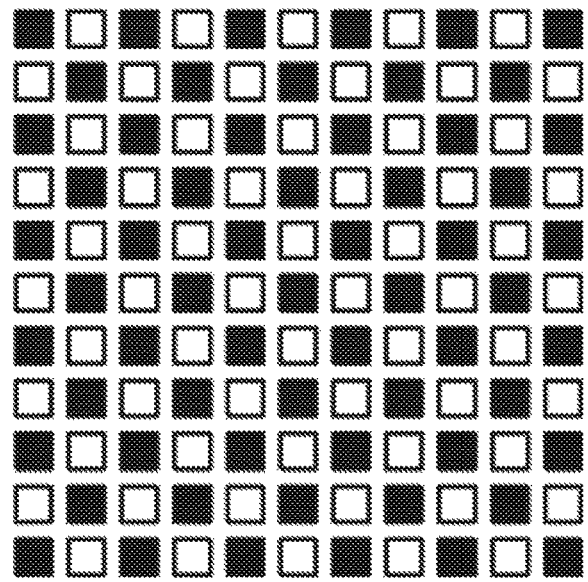
FIG. 7 illustrates a structure made up of electrode squares.
Figure 8:
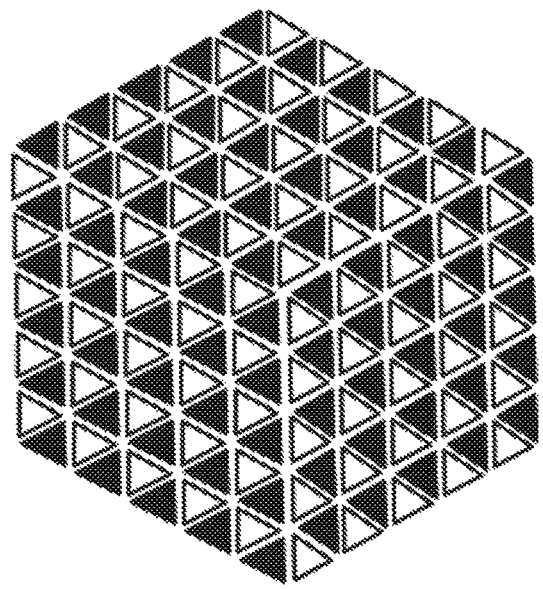
FIG. 8 illustrates a structure made up of isosceles triangles.

The invention now proposes that the usually planar detector electrode of a Faraday detector for measuring the currents of charged, free-flying particles shall be resolved into a large number of fine structural elements with a bipolar arrangement, for example a bipolar line grid, as can be seen in FIG. 4, or in square or triangular structural elements, as in FIGS. 7 and 8. The structural elements should form two bipolar groups, where neighboring structural elements should belong to opposite groups. The electrodes which belong together are shown in the same shading in FIGS. 4, 7 and 8. The structural elements are preferably applied to an insulating substrate (support), for example electronic circuit boards or ceramic plates.

FIG. 4 shows the detection electrode of a Faraday detector according to the invention in which the structural elements are linear electrodes of a bipolar line grid. The ends of the linear electrodes are brought together in two groups (15) and (16). The two groups (15) and (16) are each connected to one of the voltage supplies (21) and (22) and to one of the measuring devices (19) and (20) for electric currents.

Figure 5:
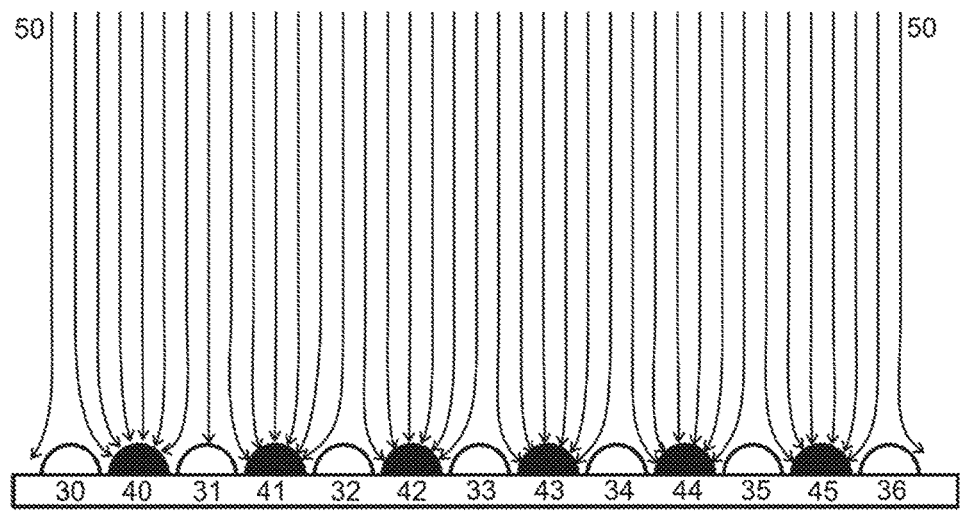
FIG. 5 depicts how incoming particles (50) are deflected just in front of the detector electrode by the electric field which is built up by a potential difference between the group of electrodes (30 to 36) and the group of electrodes (40 to 45). This deflection causes them to impinge practically only on the electrodes of group (40 to 45). If the structuring is fine enough, the image charges built up by the approaching particles are practically the same in both groups of electrodes.

Between the linear electrodes of the two groups (15) and (16), a potential difference is applied which generates an electric field that deflects charged particles laterally (here: parallel to the detector plane and orthogonal to the linear electrodes). A particle cluster which approaches the detector electrode induces the same image currents in the two groups (15) and (16) of linear electrodes before it impinges. As is depicted in FIG. 5, however, shortly before the incoming cluster particles impinge, they are deflected by the potential difference between the linear electrodes (30-36) and (40-45) in such a way that they hit only the structural elements of one polarity, i.e. the linear electrodes (40-45).

The currents of the two groups (15) and (16) of linear electrodes are each measured separately in the measuring devices (19) and (20) as functions of time and subtracted from each other. This means that the curves of the image currents which form in both groups (15) and (16) in practically the same way are subtracted from each other, leaving a current-time curve which corresponds to the pure particle current. The subtraction can be performed in an analog circuit or after the currents have been converted into digital data in a digital circuit (arithmetic logic unit). The circuits are not shown in FIG. 4. The analog circuits, which may comprise pre-amplifiers, differential amplifiers or A/D converters, are preferably arranged in the vicinity of the linear electrodes (15) and (16), preferably on the back of a support whose front contains the linear electrodes (15) and (16). It is also preferable that the circuits arranged on the back are electrically screened by a housing.

The width of the structure and the separation of the structural elements (e.g. the linear electrodes in FIG. 4) are chosen so that the laterally deflecting electric field does not penetrate to any great depth into the space in front of the detection electrode. The width of the structure and the separation of the structural elements here are preferably less than 1000 µm, most preferably less than 500 µm and particularly between 50 µm and 250 µm. They can also be less than 50 µm and particularly less than 10 µm, however. The distance to which the deflecting electric field extends into the space is equivalent to approximately once to twice the separation of the structural elements. The detector surface can be almost completely covered by the structural elements (FIG. 5). It is also possible to have gaps between the structural elements, where the width of the gaps corresponds approximately to the structural width of the structural elements (FIG. 4).

Figure 6:
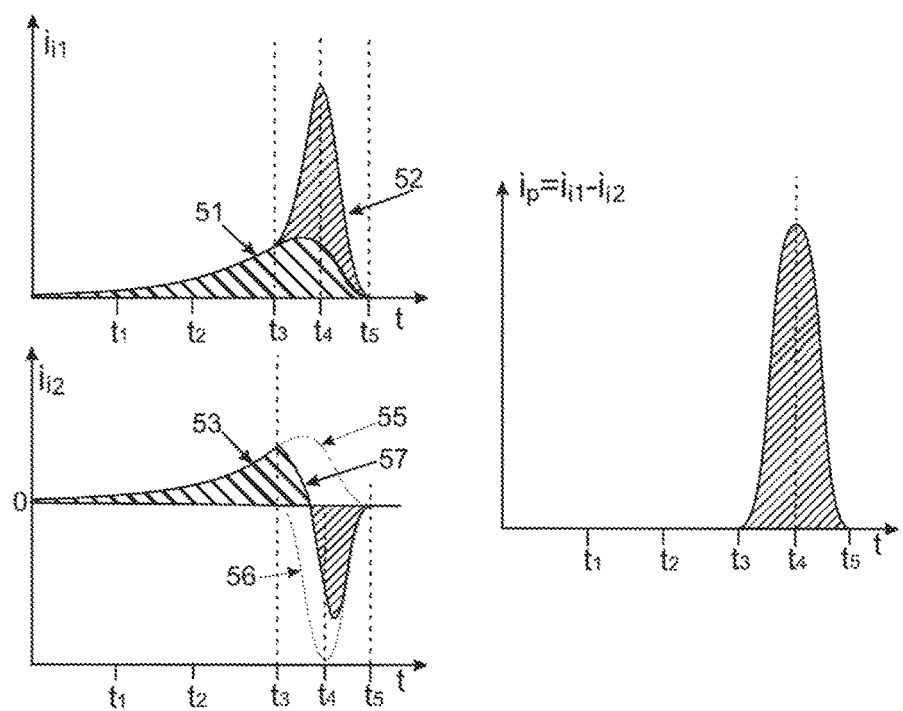
FIG. 6 shows the effect of the invention. A grid with a bipolar structure is used as the detector electrode, for example a bipolar grid according to FIG. 4 with measuring device (19) to measure the current $i_{i1}(t)$ and measuring device (20) to measure the current $i_{i2}(t)$. A cluster of ions with charge +q approaches the detector electrode and generates image currents (51) and (53) in both groups of electrodes in the same way.

FIG. 6 illustrates the operating principle of the invention in detail. The detector electrode here is a grid with a bipolar structure, for example the bipolar line grid according to FIG. 4, with the measuring device (19) to measure the first current profile $i_{i1}(t)$ of the first group of electrodes (15) and with the measuring device (20) to measure the second current profile $i_{i2}(t)$ of the second group of electrodes (16). A cluster of positive ions with charge +q approaches the detector electrode and generates image current profiles (51) and (53) in both groups of electrodes in the same way. As is shown in FIG. 5, the individual positive ions are, however, deflected at the last moment toward the group of electrodes at a negative potential (15), which are connected to the measuring device (19), however.

The two diagrams on the left-hand side of FIG. 6 show the current profiles measured at the two measuring devices (19) and (20), one below the other. The top diagram shows the current profile $i_{i1}(t)$ at the group of electrodes (15), onto which the ions are deflected.

As has already been shown in FIG. 3, an image current profile (51) forms which corresponds only to half the charge +q/2 of the cluster when integrated over time, however. At time $t_3$, when the first ions impinge on the electrode group (15), the neutralization of the image charge starts, for which only half the ion current is needed, however. The other half of the ion current flows away via the measuring device (19) and in total gives the current profile of curve (52), where the finely hatched area belongs to the ion current and the coarsely hatched area to the image current. The precise form of the current profile depends on the ion distribution in the cluster.

The bottom diagram $i_{i2}(t)$ shows that an image current with the profile (53) is also formed in the group of electrodes (16) to which no ion current flows. Curve (55) depicts the build-up of the image charge as it would look if no charge were to flow back. At time $t_3$, when the first ions impinge on the other group of electrodes (15) and thus the charge of the cluster decreases, the image charge starts to flow back.

Curve (56) illustrates the return flow of the charge as it would look if no further build-up of the image charge took place. In reality, however, the build-up of the image charge and its return flow overlap, and consequently a current corresponding to curve (57) is measured in the measuring device (20). This current profile is initially positive (coarsely hatched area) and later becomes negative (finely hatched area).

If, as is proposed in the invention, the current curve $i_{i2}(t)$ of the bottom diagram is now subtracted from the current curve $i_{i1}(t)$ of the top diagram, the result is the pure ion current (particle current) $i_p(t)=i_{i1}(t)-i_{i2}(t)$, as shown in the right-hand diagram, because the image current profiles disappear completely in the difference. As a reminder: It is precisely this particle current profile $i_p(t)$ which the invention seeks to measure.

There are several embodiments for the structuring of the detector electrode. The simplest form is that of a bipolar line grid, as shown in FIG. 4. To avoid all microphonic effects, it is best to construct the grid from conductive tracks on a solid, insulating substrate. The finer the grid rods and the spaces between them, the lower can be the setting for the voltage difference to deflect the charged particles. The image current profiles in the structural elements of both polarities then become more and more similar because the perturbations caused by the deflection of the particles become less and less.

It must be noted here that, instead of a bipolar line grid on an insulating substrate, it is also possible to use an unsupported bipolar Bradbury-Nielsen shutter. This has the advantage that the gas stream of filtered air (or nitrogen) which is often used in a mobility spectrometer can flow unhindered through the grid toward the ions. In addition, these grids can be switched to allow passage so that the particles can flow through the grid to a second detector, for example a mass spectrometer.

With a grid on an insulating substrate, the gas stream can also be allowed to pass through if the substrate has a pattern of fine holes.

Other embodiments for detection electrodes with bipolar structures are depicted schematically in FIGS. 7 and 8: The pixel-like squares and the triangles can be applied to a circuit board, but must be provided with supply leads from the back passing through the circuit board. The corners of the pixel-like elements can be beveled or rounded. Further possible embodiments are intertwined spirals or different types of labyrinths (with circular as well as rectangular structures). If the pixel-like elements are arranged on a support, the pixel-like elements of one polarity can be connected by conductive tracks in an insulated layer on a circuit board, while the pixel-like elements of the other polarity are connected in a different layer of the circuit board which is insulated from the first layer.

In principle, the structural elements of the detection electrode can be applied to circuit boards, to ceramic or to any other insulators. It is advantageous to have grooves in the substrate between the conducting electrodes in order to avoid leakage currents and charging by impinging particles. Instead of using grooves, the surfaces of the substrates can be coated with a high-resistance material. Although a small permanent current of five picoamperes, for example, then flows, this is basically harmless; a positive effect is that all types of electric charging are prevented.

If the areas of the structural elements of the two polarities are not precisely the same size, or if the deflection of the particles generates a slight asymmetry in the image currents, it is possible to introduce a weighting w when subtracting the two currents: $i_p(t)=i_{i1}(t)-w \times i_{i2}(t)$. The weighting w is selected so that a current profile is formed which is as undistorted as possible.

The method has been described here for an ion mobility spectrometer by way of example. This example should not have a limiting effect here, however. In principle, the current of clusters of any charged particles which fly onto a detector electrode can be measured with this invention without the distortions caused by the image currents. To provide another example, the electrons produced by ions in a multichannel plate (MCP) and measured by a detector plate can be measured in time-of-flight mass spectrometers in a similar way without the interfering image currents.

The invention claimed is:

1. A Faraday detector to measure the electric current profile of clusters of electrically charged particles, comprising:
   a detector electrode having structural elements in a bipolar arrangement of two groups, where neighboring structural elements have opposite polarities and structural elements with the same polarity are electrically connected, and bordering a gas-filled or evacuated space;
   at least one voltage supply which is connected with the two groups of structural elements and supplies the two groups of structural elements simultaneously with different electric potentials such that charged particles originating from the space are substantially all deflected onto one of the two groups of structural elements having one polarity; and
   a set of measurement electronics which is configured to separately measure current profiles at the structural elements of both polarities and to generate a differential signal by subtracting the current profiles to leave only a particle current profile.

2. The Faraday detector according to claim 1, wherein the detector electrode is a bipolar line grid.

3. The Faraday detector according to claim 1, wherein the detector electrode has a pixel-like structure or a mosaic structure.

4. The Faraday detector according to claim 1, wherein the detector electrode has a structure of concentric circles or spirals or a labyrinthine structure.

5. The Faraday detector according to claim 1, wherein the detector electrode is planar.

6. The Faraday detector according to claim 1, wherein the structural elements are arranged on a support.

7. The Faraday detector according to claim 6, wherein the support has an insulating or high-resistance conducting surface.

8. The Faraday detector according to claim 1, wherein the structural elements of the detector electrode are mechanically unsupported.

9. The Faraday detector according to claim 1, wherein the measurement electronics comprises current-to-voltage converters and a differential amplifier connected to the current-to-voltage converters for generating the differential signal.

10. The Faraday detector according to claim 1, wherein the measurement electronics comprises two analog-to-digital converters for converting the current profiles into two separate digital data streams, from which the differential signal is generated by a digital circuit.

11. The Faraday detector according to claim 1, wherein the width and separation of the structural elements are less than 1000 μm.

12. The Faraday detector according to claim 11, wherein the width and separation of the structural elements is between 50 and 250 μm.

13. A ion mobility spectrometer, comprising a Faraday detector according to claim 1.

14. A mass spectrometer, comprising a secondary-electron multiplier for generating electrons and a Faraday detector according to claim 1 for detecting the electrons generated in the secondary-electron multiplier.

15. The mass spectrometer according to claim 14, wherein the secondary-electron multiplier is a multichannel plate.

16. The mass spectrometer according to claim 15, wherein the mass spectrometer is a time-of-flight mass spectrometer.

17. A method for the measurement of the electric current profile of free-flying clusters of electrically charged particles which impinge on a Faraday detector electrode, wherein:
the detector electrode comprises a number of structural elements in a bipolar arrangement, where neighboring structural elements have opposite polarities and all structural elements of the same polarity are connected together;
a voltage is simultaneously applied between the two groups of structured elements of different polarities so that shortly before the incoming particles impinge, they are substantially all deflected in such a way that they hit only one of the two groups of structural elements having one polarity;
current profiles at the structural elements of both polarities are each measured separately; and the two current profiles are subtracted from each other, where the image current profiles which are formed in both groups of structural elements in practically the same way are subtracted from each other and a current profile is obtained which corresponds to a pure particle current.

18. The method according to claim 17, wherein a weighting is carried out when the two current profiles are subtracted by applying a weighting factor to one of the two current profiles prior to the subtraction, the weighting factor being selected to minimize distortion in a resulting current profile.

19. The method according to claim 17, wherein the free-flying particle clusters are ions in a mobility spectrometer.

20. The method according to claim 17, wherein the free-flying particle clusters are electrons which are generated by ions in a multichannel plate in a mass spectrometer.

21. The method according to claim 17, wherein the detector electrode is a bipolar line grid.

22. The method according to claim 17, wherein the detector electrode is a pixel-like structure or a mosaic structure.

23. The method according to claim 17, wherein the detector electrode has a structure of concentric circles, concentric spirals or a labyrinthine structure.

* * * * *